(12) United States Patent
DeSilva et al.

(10) Patent No.: US 10,589,010 B2
(45) Date of Patent: Mar. 17, 2020

(54) REDUNDANT-IMPELLER ARTIFICIAL HEART

(71) Applicants: Peter DeSilva, Rancho Santa Margarita, CA (US); Steve Smith, Trabuco Canyon, CA (US)

(72) Inventors: Peter DeSilva, Rancho Santa Margarita, CA (US); Steve Smith, Trabuco Canyon, CA (US)

( * ) Notice: Subject to any disclaimer, the term of this patent is extended or adjusted under 35 U.S.C. 154(b) by 0 days.

(21) Appl. No.: 15/405,183

(22) Filed: Jan. 12, 2017

(65) Prior Publication Data

US 2018/0193541 A1 Jul. 12, 2018

(51) Int. Cl.
*A61M 1/10* (2006.01)
*A61M 1/12* (2006.01)

(52) U.S. Cl.
CPC ........ *A61M 1/1012* (2014.02); *A61M 1/1008* (2014.02); *A61M 1/10* (2013.01); *A61M 1/101* (2013.01); *A61M 1/1029* (2014.02); *A61M 1/1031* (2014.02); *A61M 1/1055* (2014.02); *A61M 1/127* (2013.01); *A61M 2205/17* (2013.01); *A61M 2205/8206* (2013.01); *A61M 2205/8243* (2013.01)

(58) Field of Classification Search
CPC ..................................................... A61M 1/10
See application file for complete search history.

(56) References Cited

U.S. PATENT DOCUMENTS

| | | | |
|---|---|---|---|
| 6,302,661 B1 * | 10/2001 | Khanwilkar | F04D 13/0646 415/900 |
| 2013/0331934 A1 * | 12/2013 | Kabir | A61F 2/24 623/3.11 |
| 2015/0066142 A1 * | 3/2015 | Smith | A61M 1/101 623/3.13 |

* cited by examiner

*Primary Examiner* — Jacqueline Woznicki
(74) *Attorney, Agent, or Firm* — Roy A. Ekstrand

(57) ABSTRACT

An artificial heart for use in a human recipient includes a housing within which a quartet of turbine pump segments are operative. The quartet of turbine pump segments is configured to provide a pair of redundant input and output turbine pump segment pairs each input and output pair being coupled by a curved passage providing a redundancy which, in turn, enhances the safety factor provided by the artificial heart. A controller is powered by a rechargeable battery and is operative to apply appropriate drive signals to the motor drives of the turbine pump segments. The battery may be implanted along with the controller to avoid the need for any external connections to the artificial heart. An inductively coupled battery charger for use outside the recipient's body is positioned proximate the battery charger to provide inductively coupled charging for use in driving the artificial heart.

4 Claims, 10 Drawing Sheets

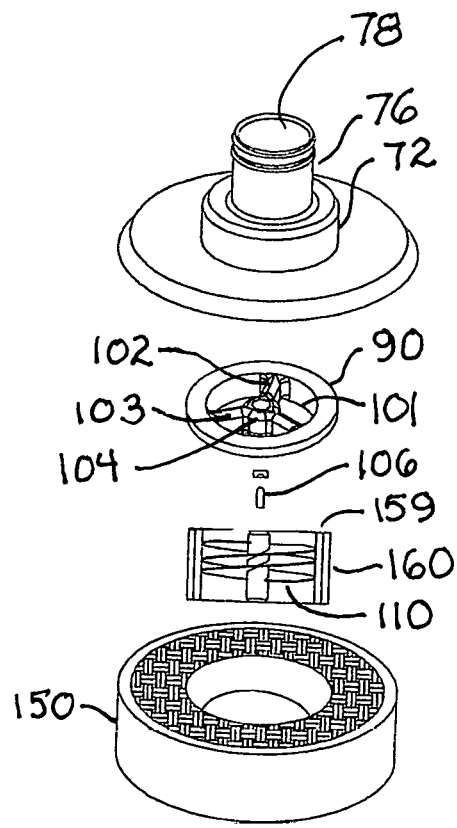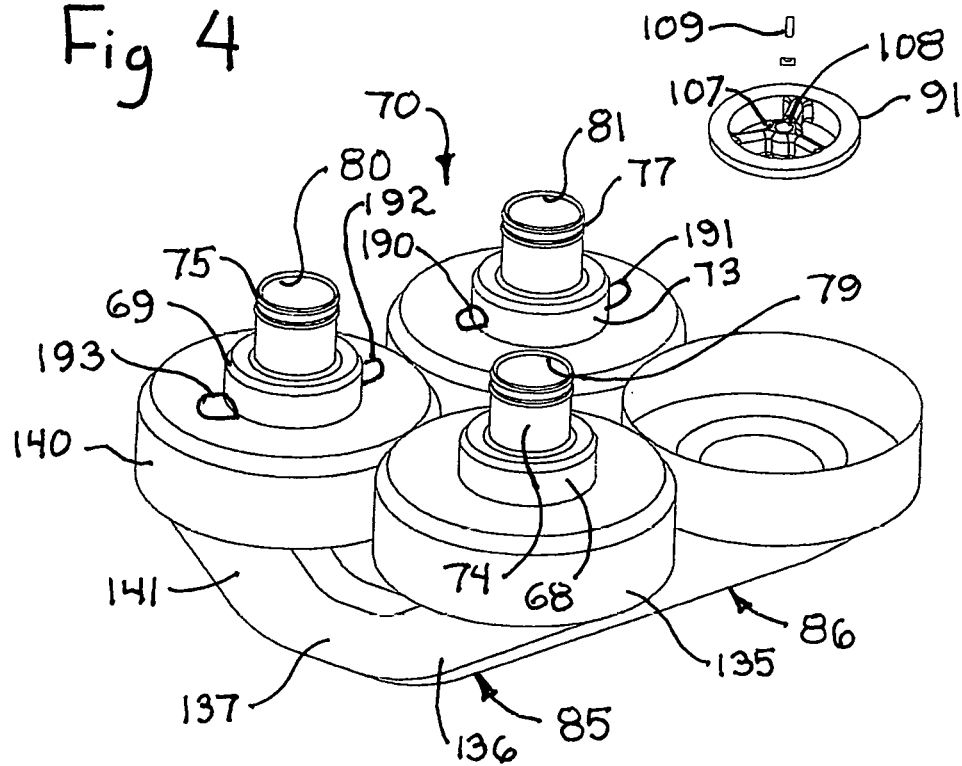
Fig 4

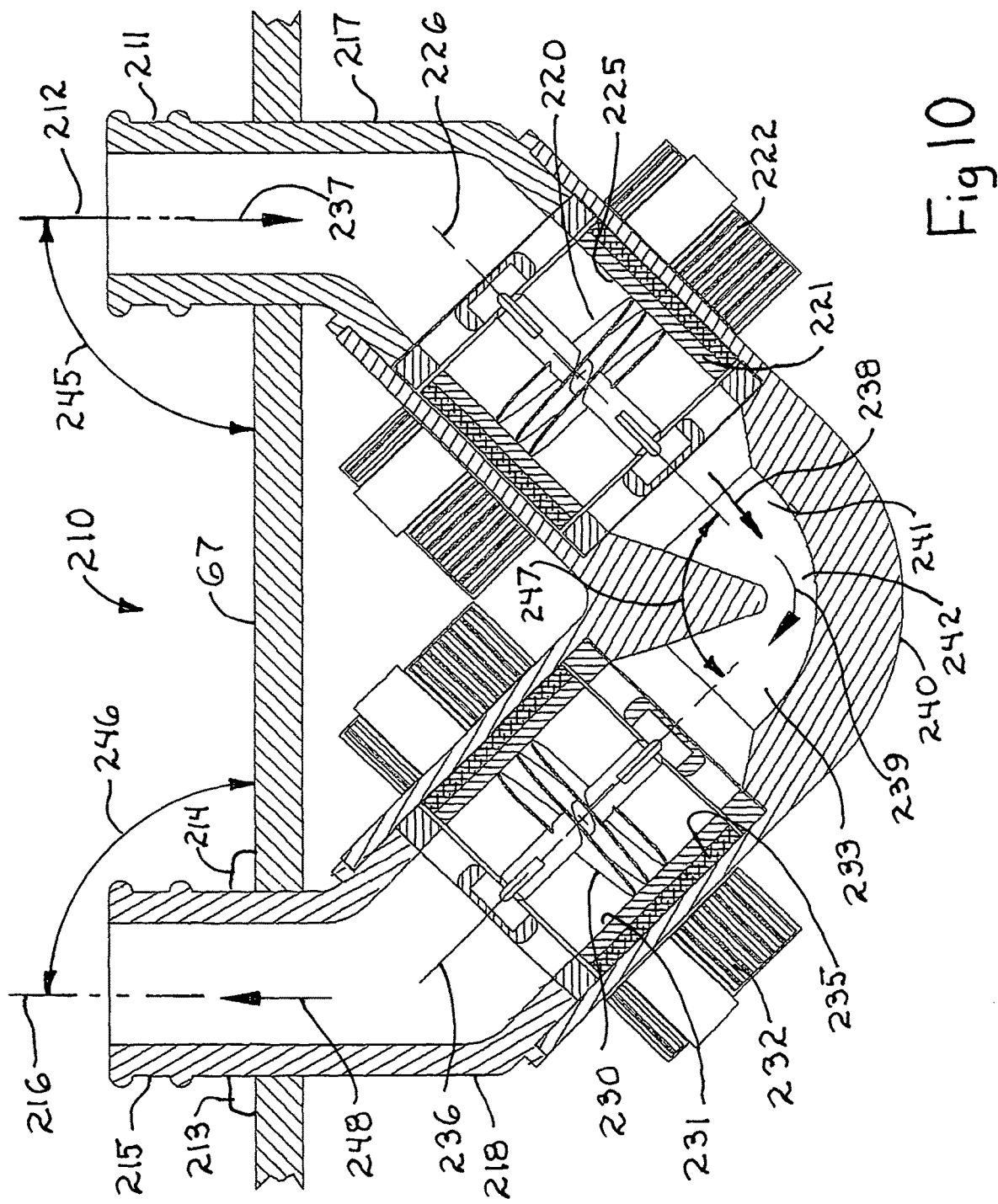

REDUNDANT-IMPELLER ARTIFICIAL HEART

This invention relates generally to apparatus for sustaining and continuing life for patients having failing or failed hearts and particularly to artificial heart replacement devices used therein. This invention also further relates to U.S. Pat. No. 9,314,559, issued to Steve Smith and Peter DeSilva, entitled FOUR CHAMBER REDUNDANT-IMPELLER ARTIFICIAL HEART, the disclosure of which is hereby incorporated herein by reference.

FIELD OF THE INVENTION

Background of the Invention

For many years, practitioners in the medical treatment and medical device arts have endeavored to provide artificial heart devices constructed to replace a failed or failing heart within a recipient. The most basic need is the creation of a replacement pumping device which is capable of performing the basic blood pumping and circulation functions of the natural heart.

Early attempts to provide a sustainable heart replacement were severely limited by the available technologies and the state of the art at that time. Devices proved to be generally too large and unwieldy and, for the most part, impractical. With the continuing advances in the related technologies and creative arts, heart replacement devices became smaller, more reliable and, in some instances, at least partially implantable within the recipient. Such "implantable" devices have generally remained hybrid devices in that the actual pump may be implanted within the recipient while additional support apparatus remains external to the patient and remains connected to the implanted device by a plurality of connecting wires and hoses.

Because of the complexity of human body systems and the complications and consequences of heart replacement device failure, the requirements for an implantable artificial heart remain daunting. Since the long term objectives of practitioners in the medical arts include a practical implantable artificial heart that a recipient may rely upon for long periods of life independent and free of medical supervision, reliability becomes of paramount importance.

Accordingly, and by way of example, a successful artificial heart replacement device must, above all, be long lasting and reliable. The dire consequences to the device recipient brought about by device failure make this requirement all too apparent. In addition, however, the device must be small enough to be implantable within the recipient's chest and efficient enough to maintain adequate blood circulation to sustain normal life functions. The device must avoid undue stress upon the recipient's circulatory and pulmonary systems. The device must also be capable of adjusting to and compensating for different recipient activity levels and stresses. Additional requirements such as avoidance of blood cell damage by the pumping apparatus and the prevention of the blood clot forming stagnation regions make further demands upon the heart replacement device.

In addition, because such artificial heart devices are implanted within the human recipient's chest cavity, it is essential that the size, shape and orientation of the artificial heart device the conducive to the confines of the recipient's body. Accordingly, it is an important aspect of the acceptability and practical utility of such artificial heart devices that the device minimize the intrusive potential of the device implant.

One such artificial heart device which embodies great promise, is shown in the above-referenced and incorporated U.S. Pat. No. 9,314,559 which sets forth an artificial heart for use in a human recipient that includes a housing within which a quartet of turbine pump segments are operative. The quartet of turbine pump segments provides a redundancy which in turn enhances the safety factor provided by the artificial heart. A controller is powered by a rechargeable battery and is operative to apply appropriate drive signals to the motor drives of the turbine pump segments. The battery may be implanted along with the controller to avoid the need for any external connections to the artificial heart. An inductively coupled battery charger for use outside the recipient's body is positioned proximate the battery charger to provide inductively coupled charging for use in driving the artificial heart.

While practitioners in the medical treatment and medical device arts have created a virtually endless number of proposed artificial heart replacement devices, there remains nonetheless a continuing unresolved need in the art for an improved, implantable, reliable and effective artificial heart replacement device which meets the stringent, unforgiving and vital requirements and challenges posed by a truly fully functioning completely implantable heart replacement device.

SUMMARY OF THE INVENTION

Accordingly, it is a general object of the present invention to provide an artificial heart replacement device which is reliable, implantable and effective. It is a more particular object of the present invention to provide an artificial heart the is sized and shaped to readily fit within the interior of a human chest cavity and abdomen. It is a more particular object of the present invention to provide an improved artificial heart replacement device which avoids the need for external component apparatus and which signals events or anomalies within the system while shifting to backup remedial life sustaining operation.

In accordance with the present invention, there is provided an artificial heart comprising: a housing having a first input, a first output, a second input and a second output; a first turbine pump operative to flow blood from the first input to the first output; a second turbine pump operative to flow blood from the first input to the first output; a third turbine pump operative to flow blood from the second input to the second output; and a fourth turbine pump operative to flow blood from the second input to the second output. The artificial heart of the present invention includes an outer housing enclosure that defines a generally planar surface upon which the first and second inputs and the first and second outputs are supported. A first curved blood flow passage is coupled between the first and second turbine pumps and a second curved blood flow passage is coupled between the third and fourth turbine pump.

The present invention improves the art by providing an artificial heart comprising: a housing having a first input connector, a first output connector, a second input connector and a second output connector; a first turbine pump, having a first pump input coupled to the first input connector, and having a first pump output, the first turbine pump operative to flow blood from the first input connector to the first output connector; a second turbine pump, having a second pump input, and having a second pump output coupled to the first output connector, the second turbine pump operative to flow blood from the first input connector to the first output connector; a third turbine pump, having a third pump input coupled to the second input connector, and having a third pump output, the third turbine pump operative to flow blood from the second input connector to the second output connector; a fourth turbine pump, having a fourth pump input, and having a fourth pump output coupled to the second output connector, the fourth turbine pump operative to flow blood from the second input connector to the second output connector; a first curved blood flow passage coupling the first pump output to the second pump input; and a second curved blood flow passage coupling the third pump output to the fourth pump input.

The use of dual pump drives and dual turbine pumps is configured to provide pump redundancy should a pump fail. In such case, the remaining operative motor/pump drives the turbine coupled thereto with sufficient capability and circulation to maintain life in the recipient until remedial intervention may be performed. The inputs to the pumps and outputs from the pumps support sensors coupled to a dual microprocessor drive controller. Each microprocessor drive controller is operatively coupled to both of the redundant pump drive motors. Sensors are also provided to monitor the operation of each pump system. A pair of battery modules each including an inductively coupled charging device are implanted within the patient abdomen and operatively coupled to the processor controller and the drive motors. A pair of inductive battery charging modules are supported upon an abdominal belt and coupled to a source of operative electrical power. Battery charging is accomplished by inductive coupling through the body tissue between the external charging modules and the implanted battery and charger apparatus. The dual redundant micro controller is also implanted within the recipient's body.

In a preferred fabrication of the present invention artificial heart, the first and second turbine pumps as well as the third and fourth turbine pumps are arranged in series pairs within the blood flow. The turbine pumps are supported within a housing defining a pair of curved blood flow passages each blood flow passage coupling the two turbine pumps in one of the series pairs of turbine pumps. In the preferred fabrication of the present invention, each of the curved blood flow passages define venturi portions.

BRIEF DESCRIPTION OF THE DRAWINGS

The features of the present invention which are believed to be novel are set forth with particularity in the appended claims. The invention, together with further objects and advantages thereof, may best be understood by reference to the following description taken in conjunction with the accompanying drawings, in the several figures of which like reference numerals identify like elements and in which:

FIG. 4 sets forth a perspective assembly view of the present invention redundant-impeller artificial heart showing the assembly of and illustrative turbine pump segment;

FIG. 10 sets forth a section view of the alternate embodiment of the present invention redundant-impeller artificial heart taken along section lines 10-10 in FIG. 9.

DESCRIPTION OF THE PREFERRED EMBODIMENTS OF THE INVENTION

By way of overview, the use of dual pump drives and dual turbine pumps in the present invention artificial heart in each blood flow channel is configured to provide pump redundancy should a pump fail. In such case, the remaining operative motor/pump drives the turbine coupled thereto with sufficient capability and circulation to maintain life in the recipient until remedial intervention may be performed. The inputs to the pumps and outputs from the pumps support sensors coupled to a dual microprocessor drive controller. Each microprocessor drive controller is operatively coupled to both of the redundant pump drive motors. Sensors are also provided to monitor the operation of each pump system. A pair of battery modules each including an inductively coupled charging device are implanted within the patient abdomen and operatively coupled to the processor controller and the drive motors. A pair of inductive battery charging modules are supported upon an abdominal belt and coupled to a source of operative electrical power. Battery charging is accomplished by inductive coupling through the body tissue between the external charging modules and the implanted battery and charger apparatus. The dual redundant micro controller is also implanted within the recipient's body. The invention further provides curved blood flow passages in each blood flow channel to facilitate locating both input connectors and both output connectors on one common side of the artificial heart which improves the device implant in many patients.

Figure 1:
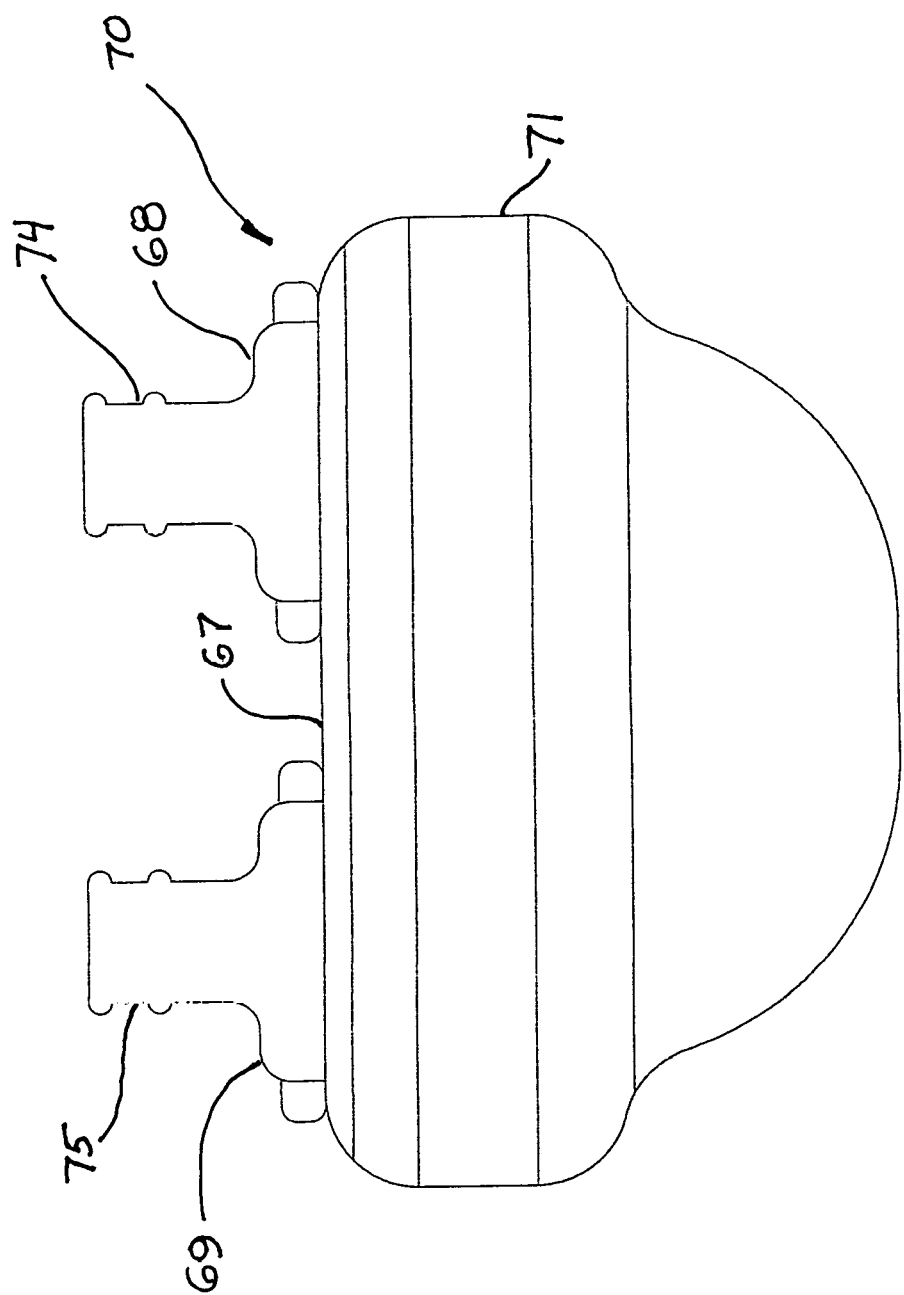
FIG. 1 sets forth a side elevation view of the present invention redundant-impeller artificial heart.
Figure 2:
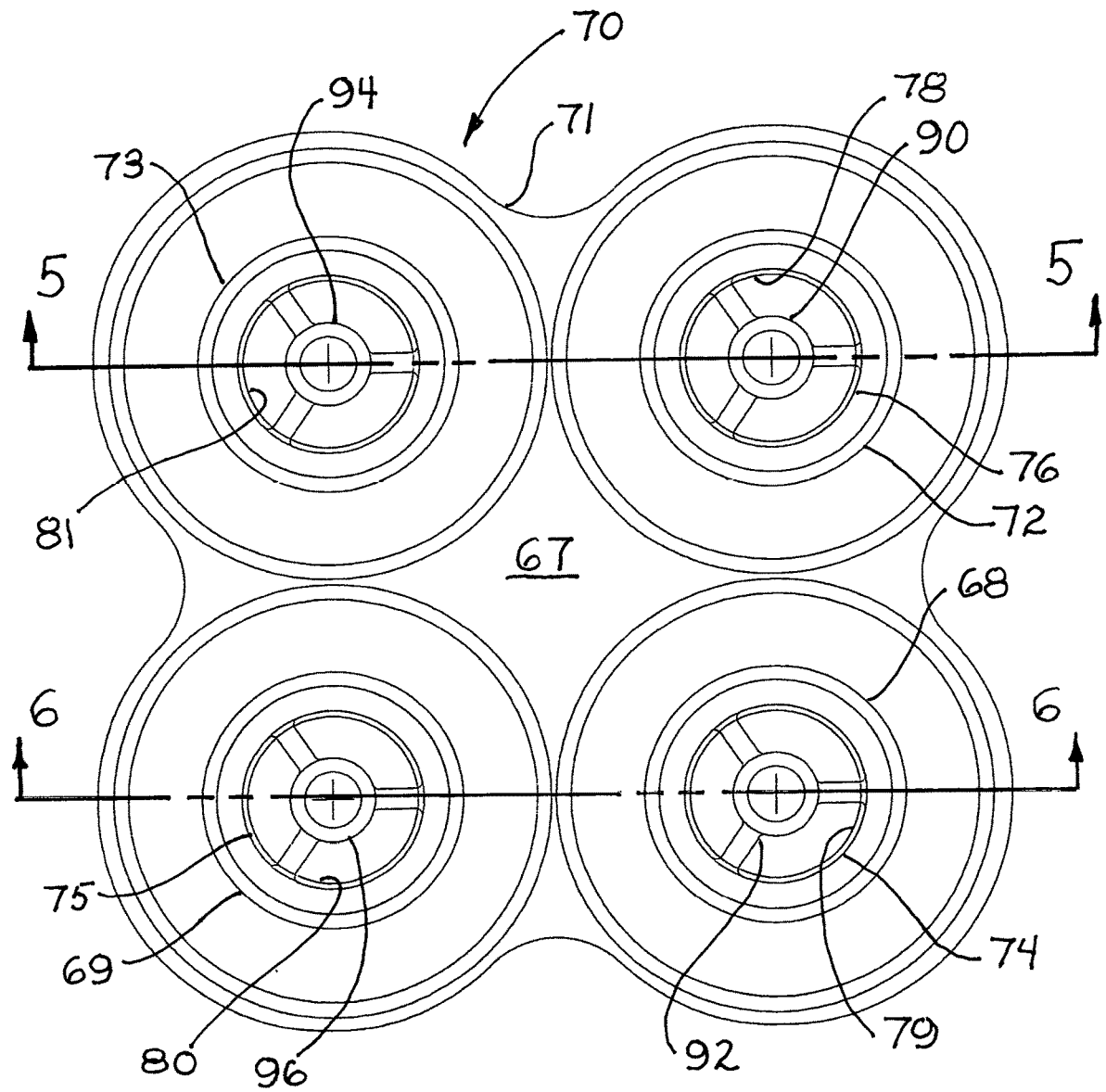
FIG. 2 sets forth a front view of the present invention redundant-impeller artificial heart showing the arrangement of input and output connectors upon a common surface.

More specifically, FIG. 1 sets forth a side view of artificial heart 70 showing housing 71 defining a common support surface 67 that, in turn, supports input end caps 68 and 72 (input end cap 72 seen in FIG. 2). common support surface 67 of housing 71 also supports output end caps 69 and 73 (output end cap 73 seen in FIG. 2). As is better seen in FIG. 2, input end caps 68 and 72 support respective input connectors 74 and 72 while output end caps 69 and 73 support respective output connectors 75 and 77, It will appreciated by those skilled in the art that the location of both input connectors 74 and 76 as well as both output connectors 75 and 77 on a common support surface 67 makes connection to the patient's circulatory system (shown below in FIG. 7) a great deal easier.

FIG. 2 sets forth a front view of redundant-impeller artificial heart 70. Artificial heart 70 is fabricated a medically approved plastic, or other implantable material. Housing 71 encloses the pump and blood flow apparatus, described below, in a smooth form fitting enclosure. Thus, within housing 71, multiple turbine pump stages operate in pairs and utilize the redundancy provided by such multiple turbine pump stages to dramatically improve reliability. In addition, as will be seen in the figures and descriptions which follow, artificial heart 70 utilizes a "flow through" design which further improves the blood flow through the pump stages and the blood flow between the pump stages to provide increased efficiency and a further protection against the stagnation or pooling of blood within the artificial heart. The latter is extremely important in that blood which is allowed to pool or stagnate within the artificial heart raises the potential for injurious or even fatal clotting of blood within the recipient's circulatory system. To avoid such problems, artificial heart 70 utilizes a direct flow through configuration through curved, preferably, venturi passages which increases blood flow velocity and does not provide areas of potential of blood stagnation or blood pooling.

Accordingly, as set forth above, artificial heart 70 having housing 71 defines a common support surface 67, which in turn, supports input end caps 68 and 72 as well as output end caps 69 and 73. End caps 68 and 72 support input connectors 74 and 76 respectively. Similarly, output end caps 69 and 73 support output connectors 75 and 77 respectively. Input connectors 74 and 76 define passages 79 and 78 respectively while output connectors 75 and 77 define respective passages 80 and 81. Input end caps 68 and 72 and output end caps 69 and 73 are secured to housing 71 utilizing an approved method of fabrication such as thermal or sonic welding. Alternatively, assembly to housing 71 may be secured utilizing adhesive attachments or, in some circumstances, medically approved fasteners. Of importance to note in determining the assembly of end caps 68, 69, 72 and 73 to housing 71 is the provision of a stable, secure and reliable attachment therebetween such that the combination thus formed becomes, in essence, a single integral housing supporting the internal turbine pumps (shown below). Turbine supports 90, 92, 94 and 96 are also seen through passages 78, 79, 81 and 80 respectively.

Figure 3:
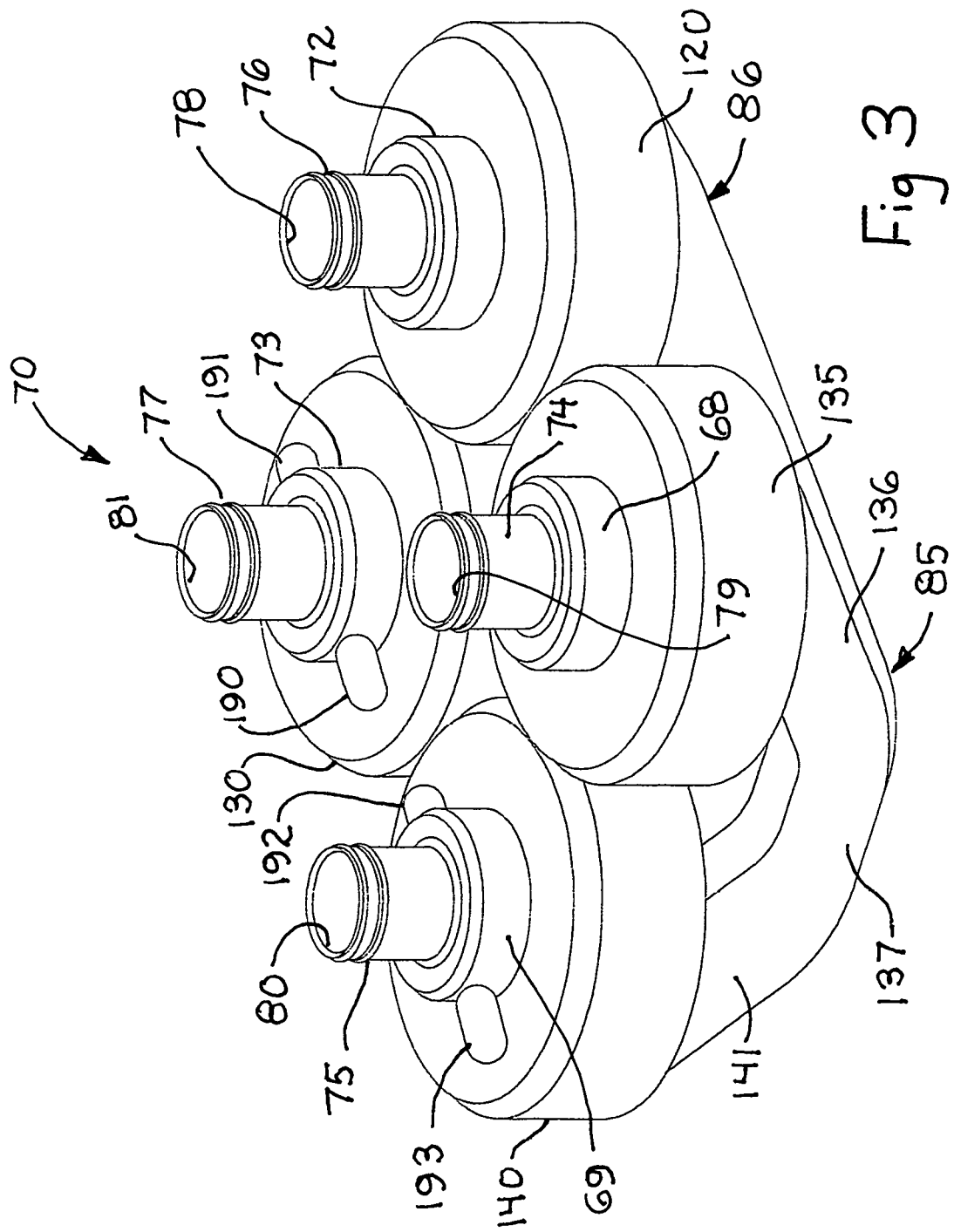
FIG. 3 sets forth a perspective view of the present invention redundant-impeller artificial heart having the outer housing removed to show the interior components.

FIG. 3 sets forth a perspective view of redundant-impeller artificial heart 70 having housing 71 removed to better show the interior components of artificial heart 70. Artificial heart 70 provides an input turbine receptacle 120 and an output turbine receptacle 130. Artificial heart 70 further includes an input turbine receptacle 135 and an output turbine receptacle 140. Input turbine receptacle 135 is coupled to output turbine receptacle 140 by a coupling passage 85. Coupling passage 85 includes a narrowing portion 136, a venturi portion 137 and an expanding portion 141. Similarly, as is better seen in FIG. 6 artificial heart 70 further includes a coupling passage 86 formed of a narrowing portion 121, a venturi portion 122 and an expanding portion 131. Input turbine receptacle supports an input end cap 72 which in turn supports input connector 76. Output turbine receptacle supports an output end cap 73 which in turn supports an output connector 77. Input turbine receptacle 135 supports an input end cap 68 which, in turn, supports and input connector 74. An output turbine receptacle 140 supports an output end cap 69 which, in turn, reports and output connector 75. Output end cap 73 further supports a pair of pressure sensors 190 and 191 similarly, output end caps 69 supports a pair of pressure sensors 192 and 193.

FIG. 4 sets forth a partial perspective partial assembly view of redundant-impeller artificial heart 70 having housing 71 removed to expose the artificial heart interior components. It will be noted that FIG. 4 shows an assembly view of an illustrative turbine pump stage operable within artificial heart 70. It will be understood that the turbine pump stages within artificial heart 70 are substantially identical. Accordingly, the illustrations and descriptions in the assembly view portion set forth in FIG. 4 will be understood to be equally descriptive of and equally applicable to the remaining turbine pump stages within artificial heart 70.

More specifically, artificial heart 70 provides an input turbine receptacle 120 and an output turbine receptacle 130. Artificial heart 70 further includes an input turbine receptacle 135 and an output turbine receptacle 140. Input turbine receptacle 135 is coupled to output turbine receptacle 140 by a coupling passage 85. Coupling passage 85 includes a narrowing portion 136, a venturi portion 137 and an expanding portion 141. Similarly, as is better seen in FIG. 6 artificial heart 70 further includes a coupling passage 86 formed of a narrowing portion 121, a venturi portion 122 and an expanding portion 131. Input turbine receptacle 120 supports an input end cap 72 which in turn supports input connector 76. Output turbine receptacle supports an output end cap 73 which in turn supports an output connector 77. Input turbine receptacle 135 supports an input end cap 68 which, in turn, supports and input connector 74. An output turbine receptacle 140 supports an output end cap 69 which, in turn, reports and output connector 75. Output end cap 73 further supports a pair of pressure flow sensors 190 and 191 similarly, output end caps 69 supports a pair of pressure sensors 192 and 193.

With reference to the assembly view portion of FIG. 4, turbine 110 is preferably fabricated to provide a helical blade progressive to form a helix. Turbine 110 further supports a cylindrical magnetic rotor 160 joined to a cylindrical metal sleeve 159 which is joined to the outer edges of turbine 110. Cylindrical magnetic rotor 160 supports a plurality of permanent magnets and together with turbine 110 forms a single preferably integrally fabricated rotating component. Thus, for example, it will be recognized that while turbine 110 may be precision-fitted within sleeve 159 of cylindrical magnetic rotor 160 due to the cylindrical structure of cylindrical magnetic rotor 160 to form a single rotating unit, in the preferred fabrication of the present invention cylindrical magnetic rotor 160 is integrally formed and molded with turbine 110. In either event, it will be recognized that the combined structure of turbine 110 and cylindrical magnetic rotor 160 forms a single integral rotating unit. The combined structure of cylindrical magnetic rotor 160 and turbine 110 are rotatably supported within the interior of input turbine receptacle 120 by a pair of turbine supports 90 and 91 positioned on each side of the rotating turbine element. The structure of turbine supports 90 and 91 is set forth below in FIG. 5. Thus, turbine support 90 includes a center hub 104 supported by a plurality of spokes 101, 102 and 103. Within hub 104, a bearing cup 105 is supported which in turn receives one end of a bearing pin 106.

Turbine support 91 is identical to turbine support 90 and thus includes a center hub 107 which receives a bearing cup 108 and bearing pin 109. During assembly, turbine support 91 receives bearing cup 108 and is inserted in turbineinput turbine receptacle 120 formed in housing 71. Thereafter, bearing pins 106 and 109 are inserted into the support shaft of turbine 110. The combined structure of turbine 110 supporting bearing pins 106 and 109 together with cylindrical magnetic rotor 160 is then inserted into turbineinput turbine receptacle 120. Turbine support 90 is then fitted within turbineinput turbine receptacle 120 such that bearing pin 106 is received within bearing cup 105. The remaining turbine segments are each assembled within their respective turbine receptacles into housing 71. Once the turbine and magnetic rotor combination have been assembled within housing 71, end caps 68, 69, 72 and 73 are joined to their respective turbine receptacles. using an attachment such as thermal or sonic welding or other appropriate attachment. Once the end caps are assembled to, the structure of artificial heart 70 is complete and the resulting pump structure may be described.

Figure 5:
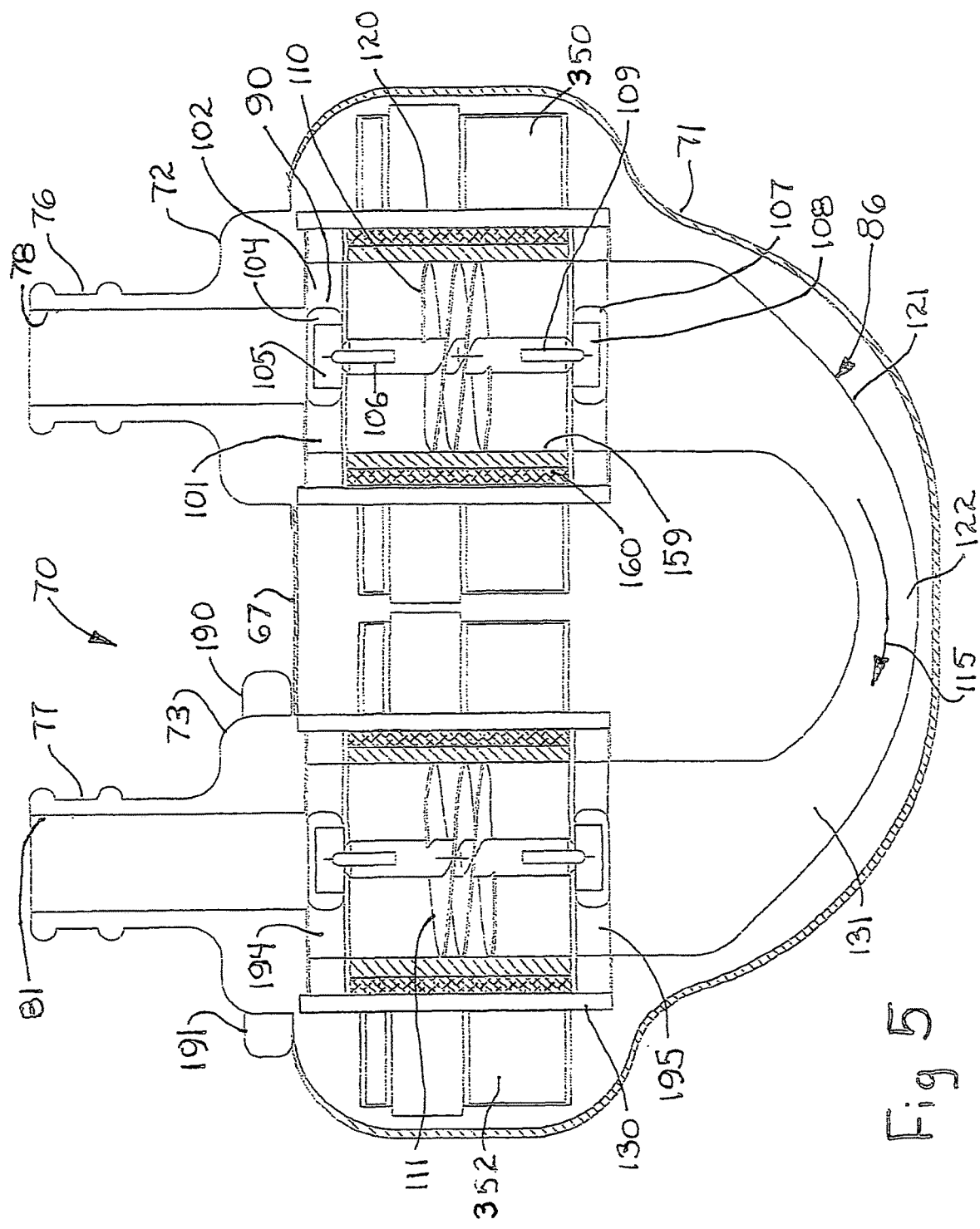
FIG. 5 sets forth a section view of the present invention redundant-impeller artificial heart taken along section lines 5-5 in FIG. 2.
Figure 6:
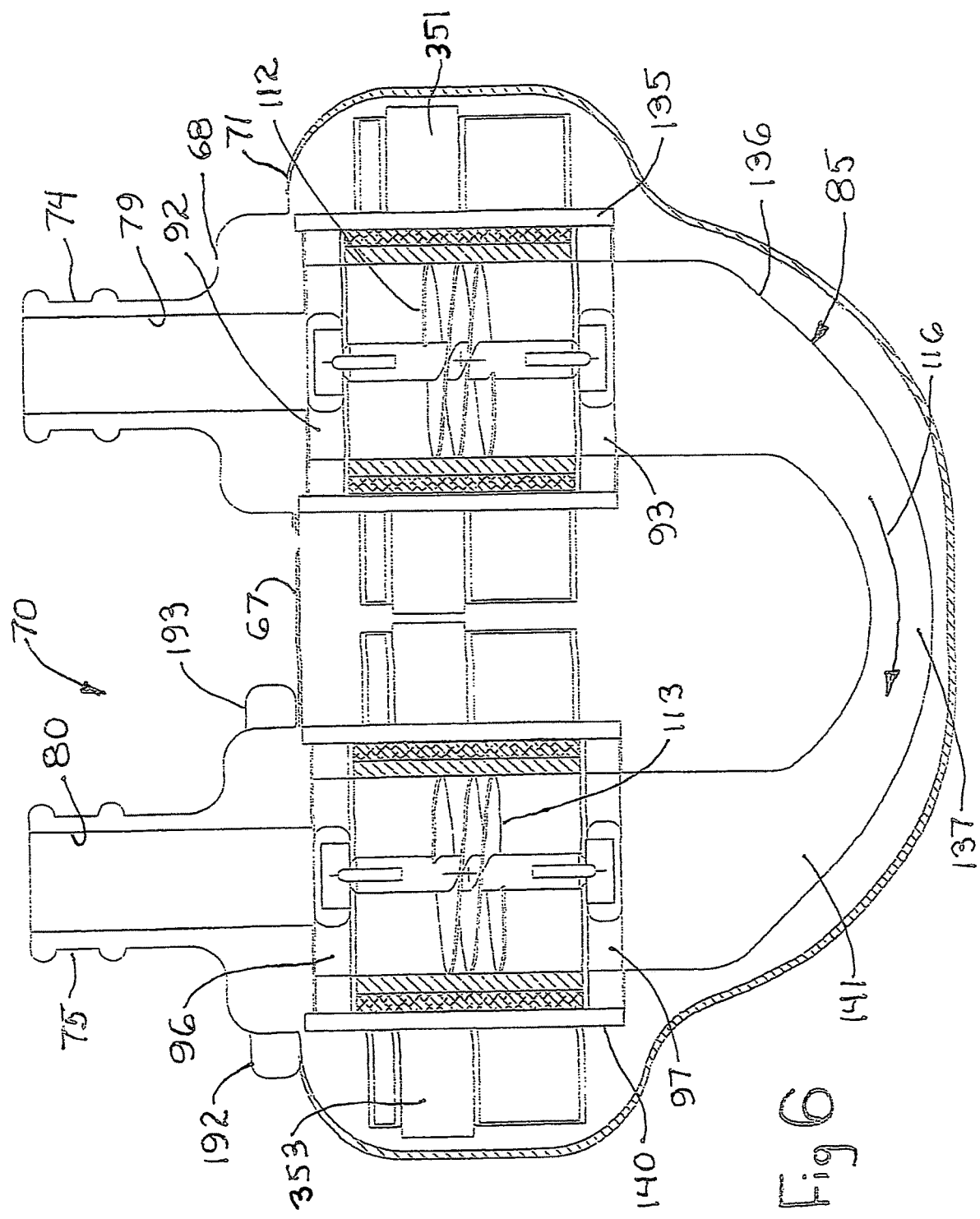
FIG. 6 sets forth a section view of the present invention redundant-impeller artificial heart taken along section lines 6-6 in FIG. 2.

FIGS. 5 and 6 set forth section views of artificial heart 70 taken along section lines 5-5 and 6-6, respectively in FIG. 2. The section views shown in FIGS. 5 and 6 show each of the identical parallel pumping apparatus forming artificial heart 70. As is set forth above, each pumping apparatus includes a pair of turbine pump segments coupled by a curved venturi coupling passage to form a redundant series coupled turbine pump pair. It will be understood that, in the preferred fabrication of the present invention, the four turbine pumps (turbines 110,111, 112 and 113 are identical.

Accordingly and with concurrent reference to FIGS. 5 and 6, the interior structure of artificial heart may be described. Housing 71 further supports a generally cylindrical drive coil 350 which encircles turbine input turbine receptacle 120. Drive coil 350 provides a motor drive coil which is supported within housing 71. Drive coil 350 is coupled to a motor controller such as microcontroller 40 set forth above in FIG. 8. Similarly, housing 71 supports a corresponding drive coil 352 which encircles output turbine receptacle 130 and a drive coil 351 which encircles input turbine receptacle 135 together with a drive coil 353 which encircles turbine receptacle 140. Drive coils 350, 351, 352 and 353 are substantially identical in fabrication.

Artificial heart 70 includes a turbine 110 and cylindrical magnetic rotor 160 joined to form a single rotating structure which is rotatably supported within turbineinput turbine receptacle 120 by turbine supports 90 and 91. Artificial heart 70 further includes a turbine 112 and magnetic rotor 161 also joined to form a single rotating structure which is rotatably supported within input turbine receptacle 135 by turbine supports 92 and 93. Artificial heart 70 further includes turbine 111 and magnetic rotor 162 joined to form a single rotating structure which is rotatably supported within output turbine receptacle 130 by turbine supports 94 and 95. Finally, artificial heart 70 further includes turbine 113 and magnetic rotor 163 joined to form a single rotating structure which is rotatably supported within turbine receptacle 140 by turbine supports 96 and 97.

As mentioned above, artificial heart 70 utilizes four turbine pump stages arranged in two series coupled pairs. It will be equally well appreciated that each of the four pump stages operative within turbine receptacles 120, 130, 135 and 140 includes a drive coil supported within housing 71 and a rotating rotor formed by the combination of a turbine and a magnetic rotor. The resulting combinations are often referred to in the art as "frameless servo motors". However, it will be apparent to those skilled in the art that other motor drive structures may be used to rotate the turbines without departing from the spirit and scope of the present invention. In accordance with an important aspect of the present invention, it will be noted that each of the four pump stages may be independently operated and controlled as to speed and output. It will be further apparent to those skilled in the art that the use of pump stages in pairs provides a redundant pump stage arrangement that allows either pump stage to continue to provide blood flow despite a failure of either pump stage.

In operation, the four pump stages of artificial heart 70 are driven in a manner described below by drive and control apparatus shown in FIG. 8. Accordingly, appropriate electrical signals are applied to drive coils 350, 351, 352 and 353 to induce rotation of magnetic rotors 160, 161, 162 and 163 which produces rotation of the rotatably supported turbines 110, 112, 111 and 113 along with their respective magnetic rotors 160, 161, 162 and 163. As is described below in greater detail, it will be noted that the rotations of turbines 110 and 111 produce a straight through curved flow path in the direction indicated by arrow 115 between input connector 76 and output connector 77. This straight through curved flow path is enhanced by the venturi coupling between turbine receptacles 120 and 130 provided by narrowing portion 121, venturi portion 122 and expanding portion 131 of curved coupling passage 86. The purpose of the venturi coupling is to increase the flow velocity between the pump turbines and further enhance the blood flow between input connector 76 and output connector 77. As a result of the straight-through blood flow thus produced, areas of stagnation and blood pooling are avoided.

In a similar fashion and for similar reasons, the blood flow from input connector 74 to output connector 75 between turbine receptacles 135 and 140 is similarly enhanced by the venturi coupling therebetween provided by narrowing portion 136, venturi portion 137 and expanding portion 141 of coupling passage 85. Once again, a direct flow-through blood flow path between input connector 74 and output connector 75 is provided. This flow path in the direction indicated by arrow 116 is enhanced by the increased flow velocity created by the venturi coupling and avoids stagnation and blood pooling.

Figure 7:
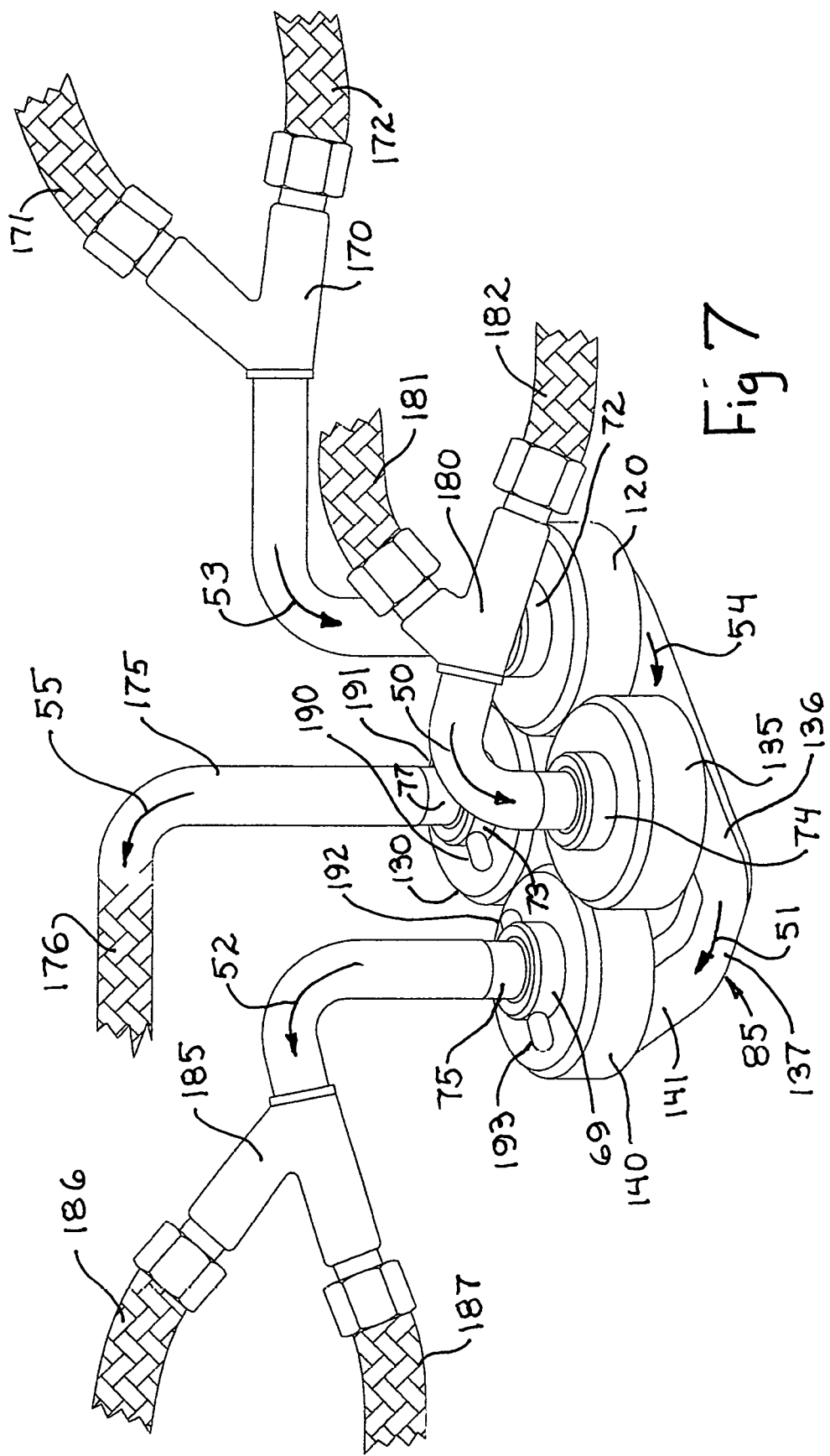
FIG. 7 sets forth a perspective view of the present invention redundant-impeller artificial heart together with the appropriate blood flow connections to be utilized within a human recipient.

FIG. 7 sets forth a perspective view of artificial heart 70 showing appropriate connections to the recipient's circulatory system. The blood flow connections are provided by medically approved tube elements and couplers. Artificial heart 70 includes a housing 71

As described above and shown in FIG. 7, artificial heart 70 is shown having housing 71 removed to better show the interior components of artificial heart 70. Artificial heart 70 provides an input turbine receptacle 120 and an output turbine receptacle 130. Artificial heart 70 further includes an input turbine receptacle 135 and an output turbine receptacle 140. Input turbine receptacle 135 is coupled to output turbine receptacle 140 by a coupling passage 85. Coupling passage 85 includes a narrowing portion 136, a venturi portion 137 and an expanding portion 141. Similarly, as is better seen in FIG. 6 artificial heart 70 further includes a coupling passage 86 formed of a narrowing portion 121, a venturi portion 122 and an expanding portion 131. Input turbine receptacle supports an input end cap 72 which in turn supports input connector 76. Output turbine receptacle supports an output end cap 73 which in turn supports an output connector 77. Input turbine receptacle 135 supports an input end cap 68 which, in turn, supports and input connector 74. An output turbine receptacle 140 supports an output end cap 69 which, in turn, supports an output connector 75. Output end cap 73 further supports a pair of sensors 190 and 191 similarly, output end caps 69 supports a pair of sensors 192 and 193.

Input connector 74 of artificial heart 70 is coupled to a split coupler 180 which in turn is coupled to the recipient's superior vena cava by a tube 181 and is further coupled to the recipient's inferior vena cava by a tube 182. Similarly, output connector 75 is coupled to a split coupler 185 which is coupled to the recipient's pulmonary arteries by a pair of tubes 186 and 187. In addition, input connector 76 is coupled to a split coupler 170 which is coupled to the recipient's pulmonary veins by pair of tubes 171 and 172. Finally, output connector 77 is coupled to a tube 176 by a coupler 175. Tube 176 is coupled to the recipient's aorta. Output connector 77 further supports a pair of sensors 190 and 191 while output connector 75 supports a pair of sensors 192 and 193. Sensors 190, 191, 192 and 193 are coupled to the artificial heart controller in the manner set forth below in FIG. 8.

In operation, as artificial heart 70 is operated, blood is drawn through input connector 74 into artificial heart 70 from the patient's superior and inferior vena cava through tubes 181 and 182 in the direction indicated by arrow 50. This blood is pumped through coupling passage 85 in the direction indicated by arrow 51 and is further pumped in the direction indicated by arrow 52 outwardly through output connector 75 and thereafter passes through split coupler 185 and tubes 186 and 187 to the recipient's lungs. The blood flows through the patient's lungs and returns to artificial heart 70 through tubes 171 and 172 and split coupler 170 in the direction indicated by arrow 53 through input connector 76. Blood is then pumped through coupling passage 86 in the direction indicated by arrow 54 and is further pumped passing outwardly through output connector 77 and coupler 175 in the direction indicated by arrow 55 to be carried by tube 176 to the recipient's aorta for distribution throughout the recipient's circulatory system.

Sensors 190 and 191 monitor the output pressure at output connector 77. Similarly, sensors 190, 192 and 193 monitor the output pressure at output connector 75. In response to variations of sensed pressure at either of outputs 75 or 77, the system controller (seen in FIG. 8) is able to adjust the operating turbine segments of the artificial heart to compensate for any failures within the quartet of turbines. In addition, it will be apparent to those skilled in the art that the drive signals applied to drive the turbine pumps may also be modulated or varied to provide a pulsitile output pressure from either or both of outputs 75 and 77. This pulsitile character imparts a more natural blood flow pattern for the recipient and may prove to be advantageous to the recipient.

Figure 8:
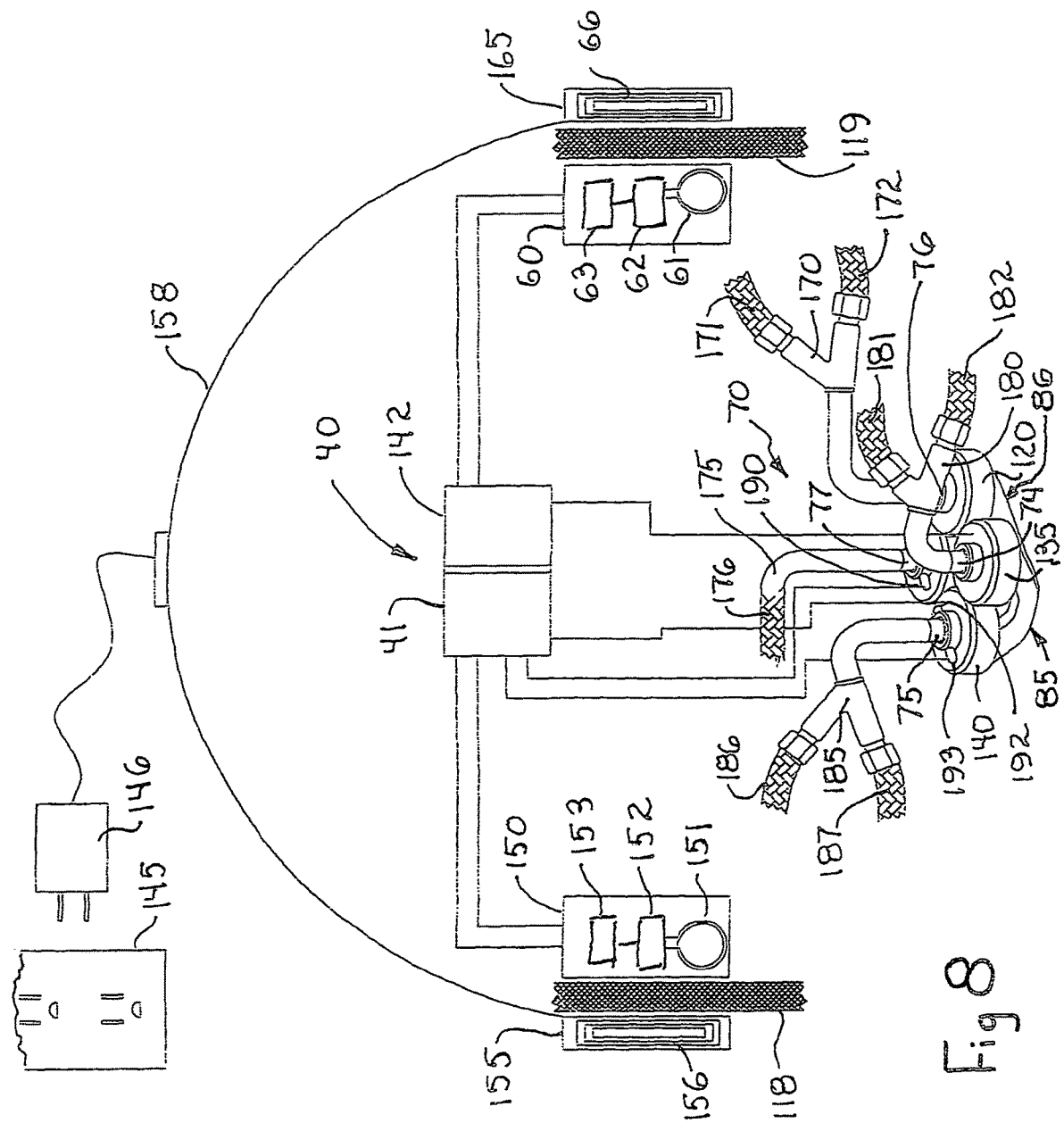
FIG. 8 sets forth a perspective view of the present invention redundant-impeller artificial heart to gather with a support system therefore.

FIG. 8 sets forth a block diagram of the present invention artificial heart in a typical surrounding environment. In the situation represented in FIG. 8, artificial heart 70 has been implanted within a host patient's body and is operatively coupled in the manner set forth above in FIG. 7 to the host patient's circulatory system. FIG. 8 further shows a microcontroller 40 also implanted within the host patient's body. Microcontroller 40 is formed of a pair of fully redundant microcontrollers 41 and 142. The redundancy of microcontrollers 41 and 142, each able to fully support the operation of artificial heart 70 provides a further measure of reliability. Microcontroller 40 further includes conventional apparatus (not shown) for communicating to the exterior of the host patient's body in order to provide alarm condition information or other required maintenance of monitoring information to an external unit (not shown). As described above, artificial heart 70 includes a plurality of sensors 190, 191, 192 and 193 situated at the respective inputs and outputs of artificial heart 70. Sensors 190 through 193 are coupled to redundant microcontrollers 41 and 142. Microcontroller 142 further includes additional sensors supported within artificial heart 70 for monitoring the performance of the servo drive apparatus therein. A pair of battery units 150 and 60 are also implanted within the host patient. Battery unit 150 includes a charging coil 151 coupled to a rectifier 152 which in turn is coupled to a battery 153. Battery unit 150 is coupled to microcontroller 141. Similarly, battery unit 60 includes a secondary coil 61 coupled to a rectifier 62 which in turn is coupled to a batter 63. By way of further similarity, battery unit 60 is operatively coupled to microcontroller 142. Thus, microcontroller 40, artificial heart 70 and battery units 150 and 60 together with appropriate wire connections therebetween are implanted within a host patient body. For purpose of illustration, FIG. 8 shows body portions 118 and 119 which represent the skin and associated tissues of the host patient body beneath which battery units 150 and 60 are implanted. Preferably units 150 and 60 are implanted near the host patient's mid section and preferably situated just beneath the patient's skin.

A charging belt 158 suitably configured to be worn by the host patient such as at or near the patient's waist supports a pair of charging units 155 and 165. Charging units 155 and 165 include respective primary charging coils 156 and 66. Primary charging coils 156 and 66 are coupled to source of alternating current power such as a conventional electrical outlet 145 via a conventional coupling adapter 146.

In operation, microcontrollers 41 and 142 monitor the plurality of sensors within artificial heart 70 and provide suitable operating power and control to the servo drives supported therein (seen in FIG. 5). Microcontrollers 41 and 142 utilize batteries 153 and 63 for operative battery supply and for power to energize the servo drive apparatus within artificial heart 70. The operative power stored within batteries 153 and 63 is provided by inductive charging utilizing charging units 155 and 165. Thus, during convenient periods, the host patient utilizes charging belt 158 by coupling to conventional electrical outlet 145 while wearing belt 158 such that primary charging coils 156 and 66 are positioned on the outside of body portions 118 and 119 respectively such that general alignment is obtained between primary charging coils 156 and 66 and secondary coils 151 and 61 respectively. Electrical power is then inductively coupled through body portions 118 and 119 to induce alternating current power within secondary coils 151 and 61. Rectifiers 152 and 62 convert the alternating current induced in secondary coils 151 and 61 to a direct current power suitable for charging batteries 153 and 63. In this manner, the user is able to replenish the battery energy as required by simply wearing charging belt 158 for a suitable time interval.

Microcontroller 40 functions using a pair of fully-redundant fully-interconnected micro controllers, each having the complete capability to control and run the entire artificial heart system and it's monitoring and charging functions. Thus, microcontrollers 41 and 142 provide inputs for two batteries, inputs for multiple pressure and Hall effect servo sensors and systems capable of monitoring multiple battery charge levels and switch between batteries. The redundancy of microcontrollers 41 and 142 includes configuration of the system such that each micro controller "sees" all its own inputs and also "sees" all inputs to the other micro controller. This redundancy includes each micro controller being capable of making compensating performance adjustments to maintain envelope system performance. However, to avoid "hunting" between the redundant micro controllers, it is preferred that small pressure variations of each pump be allowed before adjustment is made.

Microcontroller 40 further includes communication capability, such as a wireless unit, to call, or text remote locations to indicate system anomalies, failures, operating conditions, battery charge levels and other conditions. In addition, microcontroller 40 provides the capability to adjust each of microcontrollers 41 and 142 based on pressure readings and to set and maintain preset maximum and minimum pressure envelopes.

Microcontroller 40 also provides the ability of replicating the pulsitile operation characteristic of a normal human heart by introducing pre-programmed increases and decreases of pump speed to create pressure surges and lulls.

Figure 9:
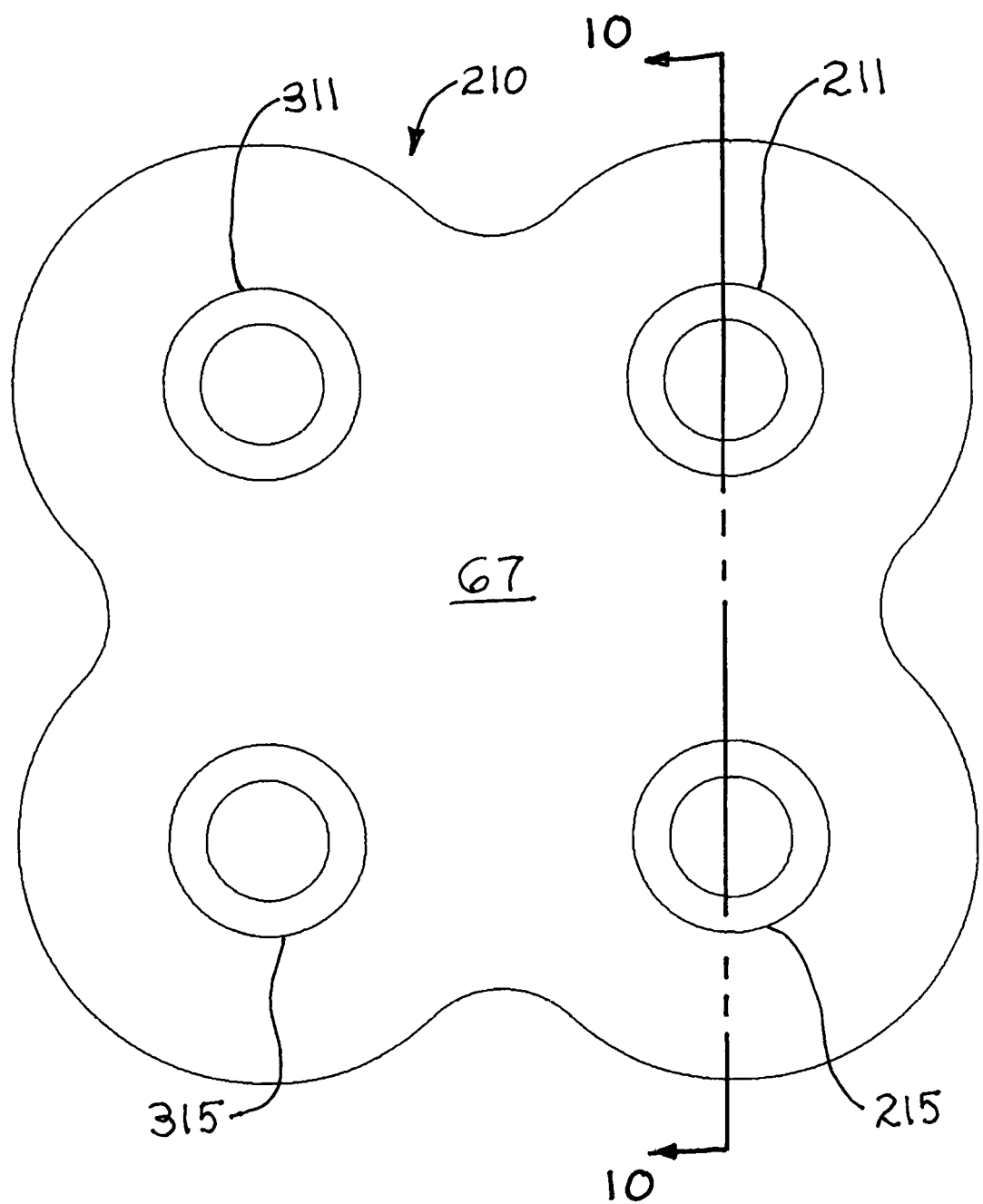
FIG. 9 sets forth a top view of an alternate embodiment of the present invention redundant-impeller artificial heart having a V-shaped coupling passage between the redundant-impellers therein.

FIG. 9 sets forth a top view of a still further alternate embodiment of the present invention redundant-impeller artificial heart generally referenced by numeral 210. By way of overview, it will be apparent that the alternate embodiment shown in FIGS. 9 and 10 is identical in function and operation to the above described embodiments in that a pair of series coupled (with respect to blood flow) turbine pumps are operative to draw blood into an input connector, flow blood through a coupling passage, that preferably includes a venturi portion, and thereafter discharge the blood flow through and output connector. Structurally, redundant-impeller artificial heart 210 differs from the above described embodiments in that the turbine pumps are coupled by a generally V-shaped coupling passage, such as coupling passage 240 (seen in FIG. 10), and that angled connectors, such as connectors 211 and 215 (seen in FIG. 10), replace the straight connectors.

More specifically, redundant-impeller artificial heart 210 includes a housing 310 supporting input connectors 211 and 311 together with output connectors 215 and 315. Housing 310 further defines a common support surface 67 through which connectors 211, 215, 311 and 315 preferably emerge at approximately right angles to common support surface 67.

FIG. 10 sets forth a section view of artificial heart 210 taken along section lines 10-10 in FIG. 9. It will be apparent to those skilled in the art that FIG. 10 sets forth a section view of the redundant turbine pair and coupling passage extending between input connector 211 and output connector 215. It will be understood that, with temporary reference back to FIG. 9, artificial heart 210 further includes a second blood flow channel having a second pair of redundant turbine pumps and a second coupling passage therebetween. It will be further apparent that the coupling channel between input connector 311 and output connector 315 is identical to the coupling channel between input connector 211 and output connector 215 set forth in section view in FIG. 10. Accordingly, it will be further understood that the descriptions and figure set forth in respect of FIG. 10 are equally illustrative of and descriptive of the identical blood flow channel extending between input connector 311 and output connector 315.

Artificial heart 210 includes an input connector 211 defining an input connector axis 212 and an output connector 215 defining an output connector axis 216. Connectors 211 and 215 preferably define respective right angles 245 and 246 with respect to common support surface 67. Artificial heart 210 includes a turbine 220 rotatably supported within a turbine receptacle 225. Turbine 220 is rotatably supported within turbine receptacle 225 and is rotatable about a turbine center axis 226. A magnetic rotor 221 is supported upon turbine 220 and is rotatable therewith. A drive coil assembly 222 is supported upon turbine receptacle 225 and provides electromagnetic energy which causes turbine 222 to rotate and provide the above described blood pumping action. The structure and operation of turbine 220 is identical to the structure and operation of turbine 255 set forth above in FIG. 12.

Artificial heart 210 further includes a turbine 230 rotatably supported within turbine receptacle 235 and rotatable about a turbine axis 236. Turbine 230 further includes a magnetic rotor 231 rotatable with turbine 230. A drive coil assembly 232 encircles turbine receptacle 235 and provides electromagnetic energy which rotates turbine 230. As mentioned above with respect to turbine 220, it will be understood that turbine 230 together with its support structure and drive coil assembly are substantially identical to the above described turbine pumps, such as turbine 110 shown in FIG. 5.

Artificial heart 210 further includes a generally V-shaped coupling passage 240 which couples blood flow from the output of turbine 220 the input of turbine 230. Coupling passage 240 includes a narrowing portion 241 followed by a venturi portion 242 and an expanding portion 233. Venturi portion 242 performs the same increase of blood flow rate described above to avoid stagnation and blood clotting problems. To accommodate the substantially perpendicular angular relationship between input connector 211 and common support surface 67, the interior end of input connector 211 defines an angle 217. Similarly, and for the same reason, output connector 215 includes an angle 218 at its interior end. Turbine axes 226 and 236 define a relative angle 247 therebetween which, in the preferred fabrication of artificial heart 210, is a right angle. However, it will be apparent to those skilled in the art, that the angular relationship between the respective axes of turbines 220 and 230 may define different angles without departing from the spirit and scope of the present invention.

In operation, blood flows inwardly through input connector 211 through turbine 220 in the direction indicated by arrow 238. Thereafter, blood flows through venturi portion 242 of coupling passage 240 in the direction indicated by arrow 239. Blood then flows through turbine 230 outwardly, in the direction indicated by arrow 248, through output connector 215.

What has been shown is a redundant-impeller artificial heart which provides an implantable housing supporting a redundant set of series coupled servo driven turbine impeller pump portions to provide blood circulation within a host patient. Extreme reliability is provided by substantial redundancy beginning with redundant turbine pump segments which are operated under the control of redundant microcontrollers. Each microcontroller is independently powered and driven by a battery unit and is configured to maintain operation in the event of failure within a servo drive or battery unit. Further redundancy is provided in that each microcontroller is configured to assume operation and control of the artificial heart should a microcontroller fail. In this manner, maximum redundancy provides corresponding maximum reliability for the inventive artificial heart apparatus. The series coupled turbine pump segments are coupled by curved venturi coupling passages to facilitate supporting all input and output connections to and from the artificial heart to be supported on a common surface for easier implant.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. An artificial heart comprising:
    a housing defining a planar common surface having a first input connector, a first output connector, a second input connector and a second output connector supported upon said common surface;
    a first turbine pump, having a first pump input coupled to said first input connector, and having a first pump output, said first turbine pump operating to induce blood flow from said first input connector to said first output connector;

a second turbine pump, having a second pump input, and having a second pump output coupled to said first output connector, said second turbine pump operating to induce blood flow from said first input connector to said first output connector;

a third turbine pump, having a third pump input coupled to said second input connector, and having a third pump output, said third turbine pump operating to induce blood flow from said second input connector to said second output connector;

a fourth turbine pump, having a fourth pump input, and having a fourth pump output coupled to said second output connector, said fourth turbine pump operating to induce blood flow from said second input connector to said second output connector;

a first curved blood flow passage coupling said first pump output to said second pump input; and a second curved blood flow passage coupling said third pump output to said fourth pump input.

2. The artificial heart set forth in claim 1 wherein said first and said second turbine pumps are coupled by said first curved blood flow passage in series and said third and said fourth turbine pumps are coupled by said second curved blood flow passage in series.

3. An artificial heart comprising:

a housing having a common surface, a first input connector upon said common surface, a first input turbine receptacle, a first output turbine receptacle, a first output connector upon said common surface, and a first curved U-shaped coupling passage between said first input turbine receptacle and said first output turbine receptacle, said housing further having a second input connector upon said common surface, a second input turbine receptacle, a second output turbine receptacle, a second output connector upon said common surface, and a second curved U-shaped coupling passage between said second input turbine receptacle and said second output turbine receptacle;

a first turbine pump, defining a first turbine axis of rotation, supported within said first input turbine receptacle, said first turbine pump operating to induce blood flow from said first input connector through said first curved U-shaped coupling passage and through said first output connector;

a second turbine pump, defining a second turbine axis of rotation, supported within said second output turbine receptacle said second turbine pump operating to induce blood flow from said first input connector through said first curved U-shaped coupling passage and through said first output connector;

a third turbine pump, defining a third turbine axis of rotation, supported within said second input turbine receptacle, said third turbine pump operating to induce blood flow from said second input connector through said second curved U-shaped coupling passage and through said second output connector; and a fourth turbine pump, defining a fourth turbine axis of rotation, supported within said second output turbine receptacle, said fourth turbine pump operating to induce blood flow from said second input connector through said second curved U-shaped coupling passage and through said second output connector.

4. An artificial heart comprising:

a housing having a common surface, first and second input connectors extending from said common connector surface, first and second input turbine receptacles, first and second output turbine receptacles, first and second output connectors extending from said common surface, and a first U-shaped coupling passage between said first input turbine receptacle and said first output turbine receptacle, said housing further having a second U-shaped coupling passage between said second input turbine receptacle and said second output turbine receptacle;

a first turbine pump, defining a first turbine axis, supported within said first input turbine receptacle, said first turbine pump operating to induce blood flow from said first input connector through said first coupling passage and through said first output connector;

a second turbine pump, defining a second turbine axis, supported within said second output turbine receptacle said second turbine pump operating to induce blood flow from said first input connector through said first coupling passage and through said first output connector;

a third turbine pump, defining a third turbine axis, supported within said second input turbine receptacle, said third turbine pump operating to induce blood flow from said second input connector through said second coupling passage and through said second output connector; and a fourth turbine pump, defining a fourth turbine axis, supported within said second output turbine receptacle, said fourth turbine pump operating to induce blood flow from said second input connector through said second coupling passage and through said second output connector.

* * * * *